United States Patent
Lal et al.

(10) Patent No.: US 7,108,137 B2
(45) Date of Patent: Sep. 19, 2006

(54) METHOD AND APPARATUS FOR SEPARATING PARTICLES BY SIZE

(75) Inventors: Amit Lal, Ithaca, NY (US); Chung Hoon Lee, Ithaca, NY (US)

(73) Assignee: Wisconsin Alumni Research Foundation, Madison, WI (US)

( * ) Notice: Subject to any disclaimer, the term of this patent is extended or adjusted under 35 U.S.C. 154(b) by 315 days.

(21) Appl. No.: 10/263,385

(22) Filed: Oct. 2, 2002

(65) Prior Publication Data

US 2004/0065599 A1    Apr. 8, 2004

(51) Int. Cl.
*B01D 43/00*    (2006.01)

(52) U.S. Cl. .................. 209/659; 210/748; 209/156

(58) Field of Classification Search ............ 209/659, 209/629, 552, 576, 570, 18, 156, 158, 160; 210/748; 204/157.42; 96/389; 95/29
See application file for complete search history.

(56) References Cited

U.S. PATENT DOCUMENTS

| | | | |
|---|---|---|---|
| 4,055,491 A * | 10/1977 | Porath-Furedi | 210/738 |
| 4,523,682 A * | 6/1985 | Barmatz et al. | 209/638 |
| 4,759,775 A * | 7/1988 | Peterson et al. | 210/708 |
| 4,877,516 A * | 10/1989 | Schram | 209/155 |
| RE33,524 E * | 1/1991 | Schram | 210/748 |
| 5,006,266 A * | 4/1991 | Schram | 210/748 |
| 5,147,562 A * | 9/1992 | Heyman | 210/748 |
| 5,164,094 A * | 11/1992 | Stuckart | 210/708 |
| 5,192,450 A * | 3/1993 | Heyman | 210/748 |
| 5,225,089 A * | 7/1993 | Benes et al. | 210/748 |
| 5,484,537 A * | 1/1996 | Whitworth | 210/748 |
| 5,527,460 A * | 6/1996 | Trampler et al. | 210/198.1 |
| 5,626,767 A * | 5/1997 | Trampler et al. | 210/748 |
| 5,665,605 A | 9/1997 | Coakley et al. | |
| 5,688,405 A * | 11/1997 | Dickinson et al. | 210/748 |

(Continued)

OTHER PUBLICATIONS

Glenn Whitworth, et al., "Particle Column Formation in a Stationary Ultrasonic Field," J. Acoust. Soc. Am., vol. 91, No. 1, Jan. 1992, pp. 79-85.

(Continued)

*Primary Examiner*—Kathy Matecki
*Assistant Examiner*—Matthew J. Kohner
(74) *Attorney, Agent, or Firm*—Foley & Lardner, LLP (57) ABSTRACT

A method and apparatus for separating a mixture of particles of various sizes in a capillary tube into groups by size using multiple forces of controlled amplitude. Ultrasonic radiation at a first selected frequency is applied to set up a standing pressure wave in the capillary tube, resulting in a first aggregating force which causes particles of all sizes to aggregate at positions within the capillary tube which correspond to nodes or anti-nodes of the standing wave. Transverse vibrations are also applied to the capillary tube. The frequency of the ultrasonic radiation is adjusted to reduce the magnitude of the first aggregating force. Inertial forces resulting from the transverse vibrations then cause the particles to separate by size. The apparatus and method allows a mixture of particles to be separated by size quickly, without requiring the use of high voltages.

26 Claims, 9 Drawing Sheets

U.S. PATENT DOCUMENTS

| | | | |
|---|---|---|---|
| 5,688,406 A * | 11/1997 | Dickinson et al. | 210/748 |
| 5,711,888 A * | 1/1998 | Trampler et al. | 210/748 |
| 5,902,489 A * | 5/1999 | Yasuda et al. | 210/748 |
| 5,912,182 A | 6/1999 | Coakley et al. | |
| 5,951,456 A * | 9/1999 | Scott | 516/195 |
| 6,055,859 A * | 5/2000 | Kozuka et al. | 73/570 |
| 6,216,538 B1 * | 4/2001 | Yasuda et al. | 73/570.5 |
| 6,221,258 B1 * | 4/2001 | Feke et al. | 210/748 |
| 6,273,262 B1 * | 8/2001 | Yasuda et al. | 209/1 |
| 6,332,541 B1 | 12/2001 | Coakley et al. | |
| 6,749,666 B1 * | 6/2004 | Meegan, Jr. | 95/29 |
| 6,786,174 B1 * | 9/2004 | Schleier-Smith | 118/50.1 |
| 6,797,158 B1 * | 9/2004 | Feke et al. | 210/97 |

OTHER PUBLICATIONS

Teruyuki Kozuka, et al., "Non-Contact Micromanipulation Using an Ultrasonic Standing Wave Field," IEEE, The Ninth Annual International Workshop on Micro Electro Mechanical Systems, 1996, pp. 435-440.

K. Yosioka, et al., "Acoustic Radiation Pressure on a Compressible Sphere," Acustica, vol. 5, 1955, pp. 167-173.

K. Yasuda, et al., "Acoustic Radiation Force on Micrometer-Size Particles," Appl. Phys. Lett., vol. 71, No. 13, 1997, pp. 1771-1773.

* cited by examiner

(b) calculated velocity

METHOD AND APPARATUS FOR SEPARATING PARTICLES BY SIZE

STATEMENT OF GOVERNMENT RIGHTS

This invention was made with United States government support awarded by the following agencies: DOD ARPA F30602-00-2-0572. The United States has certain rights in this invention.

FIELD OF THE INVENTION

The present invention relates generally to the field of separating particles by size (particle chromatography), and particularly to separating particles by size using ultrasound.

BACKGROUND OF THE INVENTION

Many fluids and other materials used in science and industry, especially biological materials, contain particles having various sizes. For example, blood contains red blood cells, white blood cells, platelets, and other components which can be distinguished by their size. Further, a wide variety of biological materials, such as cells, proteins, antibodies, and DNA, can be bound to polystyrene and latex beads of various sizes. For example, antibodies immobilized on beads of various sizes are used in integrated protein bioassays, an accepted tool of clinical medicine. Thus, a system that can separate particles by size can enable red blood cell counts, bead-based assays, and other measurements useful in medicine, and in other applications in science and industry.

A variety of techniques have been developed to separate particles by size, such as electro-osmotic flow, magnetic separations, dielectrophoretic separations, electrophoretic separations, diffusion-based separations, cantilever-binding mass-sensing assays, and acceleration techniques. However, the practical value of these prior techniques may be limited by real-world considerations such as cost, power or voltage requirements, sample volume requirements, difficulty of manufacture, complex construction, moving parts, measurement quality, reliability, and response time.

For example, a typical electro-osmotic microfluidic assay system for separating particles of varying sizes utilizes the differential mobility of the differently-sized particles in a high electric field, but this technique may require a conducting medium and high voltages. Magnetic bead separation may require the use of high currents for sufficient magnetic field production, or physical movement of external magnetic components, which may be more costly, more difficult to manufacture, and less reliable than techniques which do not require moving parts. Dielectrophoretic and electrophoretic separations both may require electrical connections to the fluid as well as a non-conducting medium and high voltages. Binding to a cantilever and detecting the resulting mass or strain change may require coating of the cantilevers with specific binding molecules, making the test instrument specific to a particular test. Thus, each of the prior art techniques for separating particles of differing sizes may have disadvantages that limit practical utility.

Particle manipulation with a projected acoustic field has been investigated by many researchers. Acoustic radiation forces generated by concave transducers have been used to concentrate particles at pressure nodes. See, for example, U.S. Pat. No. 6,332,541 to Coakley et al., which discloses an apparatus for separating particles from a fluid. However, separation of particles by size using acoustic radiation force has not been demonstrated.

SUMMARY OF THE INVENTION

The present invention provides a method and apparatus for separating by size a mixture of different size particles using ultrasound. A mixture of different size particles are first focused at nodes of a standing pressure wave in a vessel, for example a glass capillary, and then separated by an inertial nonlinear force generated by transverse vibrations in the vessel.

The present invention provides an improved system for separation of particles by size with several desirable characteristics. The invention can be embodied in designs which are easy to manufacture, and which avoid the need for moving parts, reducing cost and improving reliability. Reduced power and voltage requirements can enable portable operation using batteries or other low power sources. An integrated microfluidic system, which may be implemented on a very small scale using integrated circuit or micromechanical techniques, can allow operation using microscale amounts of liquid. An integrated microfluidic system in accordance with the invention can enable sample preparation integration, device miniaturization for ambulatory applications, power reduction for battery operation, and lower cost of bioassays.

Further objects, features and advantages of the invention will be apparent from the following detailed description when taken in conjunction with the accompanying drawings.

DETAILED DESCRIPTION OF THE INVENTION

Figure 1:
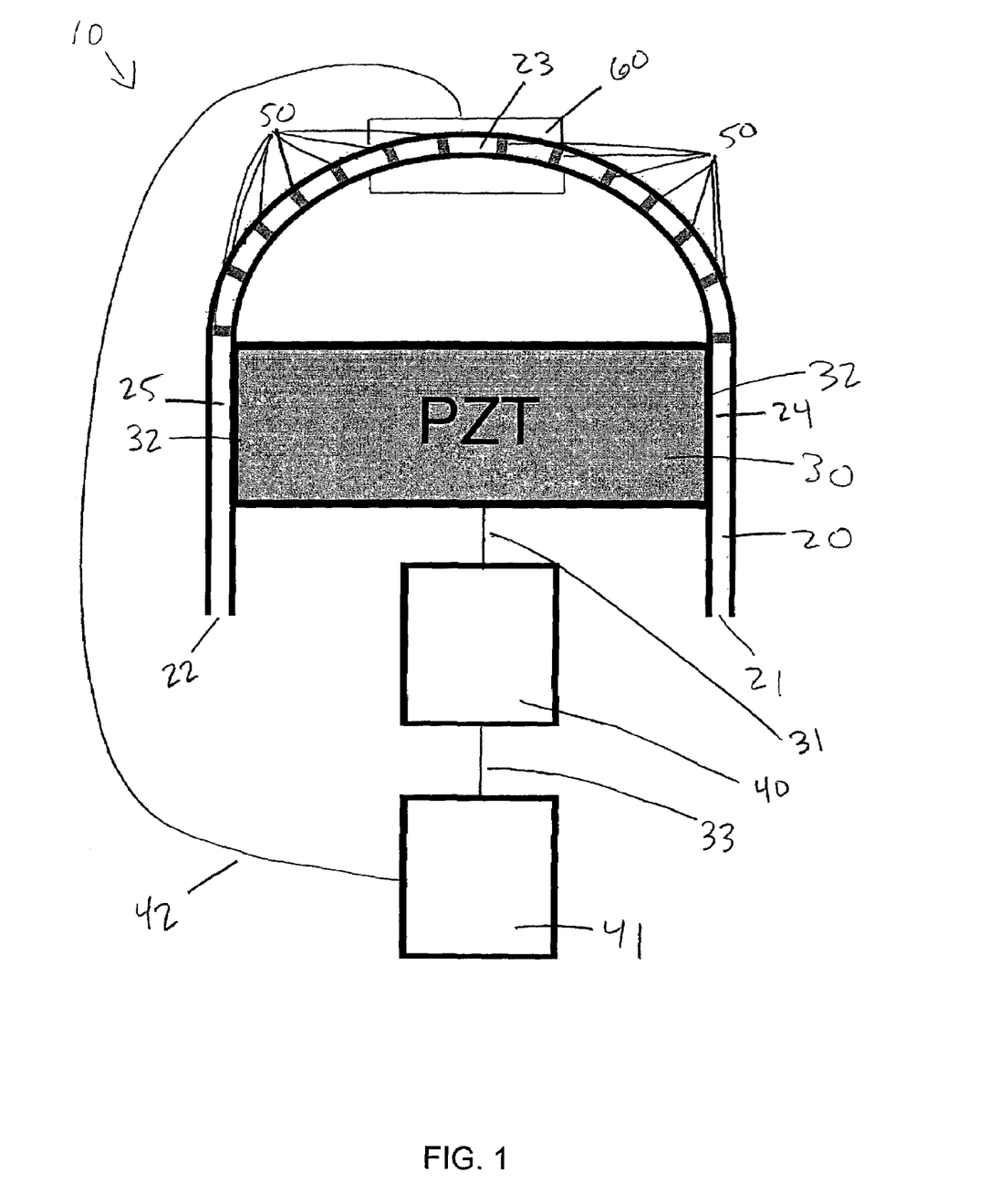
FIG. 1 is a schematic view of a preferred embodiment according to the invention.

With reference to the drawings, FIG. 1 shows a preferred embodiment of an apparatus for separating particles by size in accordance with the invention indicated generally at 10. The apparatus 10 includes a vessel 20, which may be a polyimide coated glass capillary tube having an inner diameter of about 100 μm, an outer diameter of about 200 μm, and a coated polyimide thickness of about 12 μm, of the type which is available, for example, from Polymicro Technologies, LLC of Phoenix, Ariz. In the preferred embodiment shown in FIG. 1, the vessel 20 has an input end 21, an output end 22, a curved section 23, an input section 24 between the input end 21 and the curved section 23, and an output section 25 between the curved section 23 and the output end 22. The vessel preferably also bears visible markers 50, for example litho-graphically defined evenly spaced titanium thin film markers, which may be used to assist velocity measurements and to monitor bead location in the vessel, although this is not required. The vessel 20 contains an acoustic medium, which is preferably a liquid, in which a mixture of particles of differing sizes may be suspended for separation.

The apparatus 10 further includes an acoustic transducer 30, for example a piezoelectric PZT (lead-zirconate-titanate oxide) plate roughly about 10 mm long, about 2.5 mm wide, and about 0.5 mm thick of the type which is available, for example, from Morgan Electro Ceramics, Inc. of Bedford, Ohio. A signal generator 40, of the type which is known in the art, may be used to produce a signal which is applied to the acoustic transducer 30 via electrodes 31. The electrodes 31 are preferably soldered at approximately the center of the PZT plate since a displacement node of the PZT plate is at its center, but this is not required.

The apparatus 10 may include a detector 60, for example a charged coupled device (CCD) optical detector such as model LSO-2700T3-8EPP(-S) available from Eureca Messtechnik GmbH of Köln, Germany, which may produce a signal containing information which can be used to measure the total quantity of particles when aggregated, as well as the quantity of particles of each size after separation.

The apparatus 10 may optionally include a controller 41, for example a computer of the type which is known in the art, for controlling the signal generator 40 via a control cable 33, which may be a wire, coaxial cable, optical fiber, integrated circuit conductor, radio frequency modulator/demodulator, or any other structure or apparatus for carrying control information. The controller 41 may optionally receive a signal from the detector 60 via a detector cable 42, which may be a wire, coaxial cable, optical fiber, integrated circuit conductor, radio frequency modulator/demodulator, or any other structure or apparatus for carrying measurement information. The controller 41 may adjust the output of the signal generator 40 in response to measurement information from the detector 60, for example by adjusting the frequency, amplitude, or other characteristics of the output of the signal generator.

In the preferred embodiment shown in FIG. 1, the vessel 20 is formed in a semi-circle which is wrapped around the acoustic transducer 30, such that portions of the vessel 20, for example the input section 24 and the output section 25 of the vessel, are preferably in intimate contact with the acoustic transducer 30. To promote the intimate contact between the acoustic transducer 30 and the vessel 20, each end of the acoustic transducer 30 may have a notch 32, for example a 300 μm deep trench and the input section 24 and the output section 25 of the vessel 20 may be adhesively bonded to the notches 32 on the acoustic transducer 30 using glue, for example a cyanoacrylate glue of the type which is widely available, although this is not required.

This configuration of a preferred embodiment allows easy access to the detector 60, and also decouples the acoustic boundary conditions of the apparatus 10 from those of external components. With this preferred construction, the initial aggregation of particles occurs at a predictable location in the acoustic medium, and the subsequent separation of particles by size occurs over a predictable distance in the acoustic medium.

Figure 2:
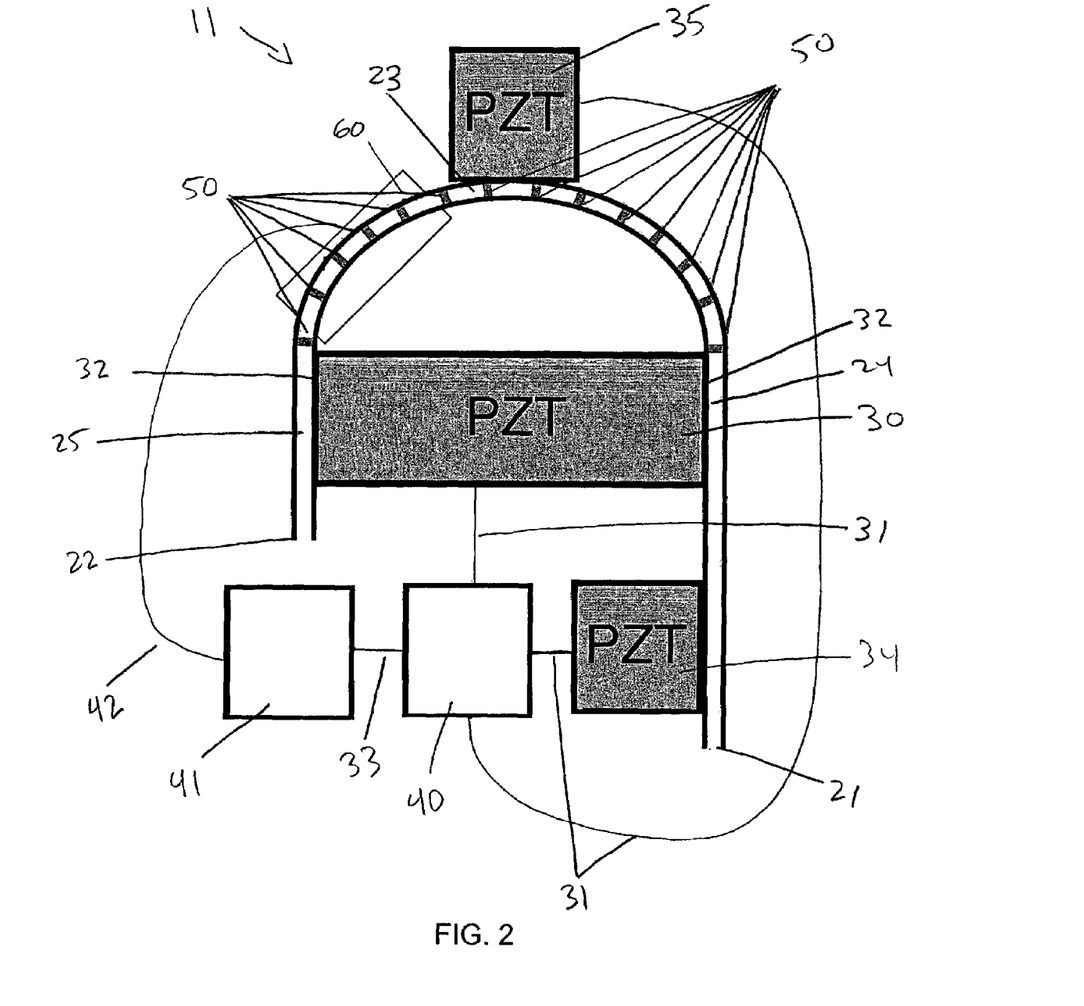
FIG. 2 is a schematic view of an alternative embodiment according to the invention.

With reference to the drawings, FIG. 2 shows an alternative embodiment of an apparatus for separating particles by size in accordance with the invention indicated generally at 11. The alternative embodiment 11 may contain a second acoustic transducer 34 and/or a third acoustic transducer 35, which may be, for example, piezoelectric PZT plates. The optional second acoustic transducer 34 and third acoustic transducer 35 may be used individually or together with the acoustic transducer 30, for example, to apply additional acoustic fields to the sample volume or to pump the sample through the apparatus.

Although it is believed that the invention operates according to the following theory of operation of the invention, this theory of operation is provided to explain the invention and not to limit the scope of the invention.

The operation of an apparatus according to the invention may be summarized as follows. First, an acoustic transducer, for example a PZT plate, stretches the vessel in the length direction, which excites the longitudinal mode of the liquid in the vessel creating a standing pressure wave that leads to particle aggregation at pressure nodes in the vessel. Second, an acoustic transducer, for example a PZT plate, excites transverse vibrations of the vessel, generating an inertial nonlinear force that separates the aggregated particles.

The basic principle of the particle aggregation is that applying a first acoustic field to excite the longitudinal mode of an acoustic medium, for example a liquid, in the vessel creates a standing pressure wave in the acoustic medium in the vessel, whereby the diffracted acoustic field from a particle leads to a nonsymmetric acoustic field around the particle. The nonsymmetric field results in a net force to move the particle. Specifically, the 2nd order pressure integrated over the particle surface results in a net force pulling the particles to acoustic nodes or antinodes depending on the acoustic contrast constant, $$A(\alpha, \sigma) = \frac{\alpha + 2(\alpha - 1)/3}{1 + 2\alpha} - \frac{1}{3\alpha\sigma^2} \quad (1)$$

where $\alpha$ is the ratio of the bead density to the medium density and $\sigma$ is the ratio of the speed of sound. For standing waves, the radiation force has been derived as, $$F_{ac} = -4\pi k d^3 \bar{\epsilon} \sin(2kx) A(\alpha, \sigma) \quad (2)$$

where k is the acoustic wave number, d is the radius of a sphere, $\bar{\epsilon}$ is the mean total energy-density, x is the distance from the pressure node and $A(\alpha,\sigma)$ is the density-compressibility factor that is given by Eq. 1. This expression is valid with $d/\lambda \ll 1$, where d is the diameter of the bead and $\lambda$ is the wavelength, a condition easily satisfied in experiments. If the particles to be separated by size are polystyrene beads, for example, since the contrast factor A of polystyrene beads is positive, the density of polystyrene is 1.05 g/cm$^3$, and the speed of sound is 2170 m/s, such beads are expected to move toward the pressure nodes ($x=n\lambda/2$, where $n=0, 1, 2, \ldots$) of the standing wave in the vessel.

The PZT plate used as an acoustic transducer in the preferred embodiment shown in FIG. 1 will have a $\lambda/2$ (half-wavelength) mode of vibration in both length and width directions, each with a resonance frequency. The resonance frequency of this mode can be approximated as $$f = \frac{c}{2L_{eff}} \quad (3)$$

where c(~3200 m/s) is the speed of sound in the PZT plate and $L_{eff}$ is the effective length or width of the PZT plate.

Figure 3:
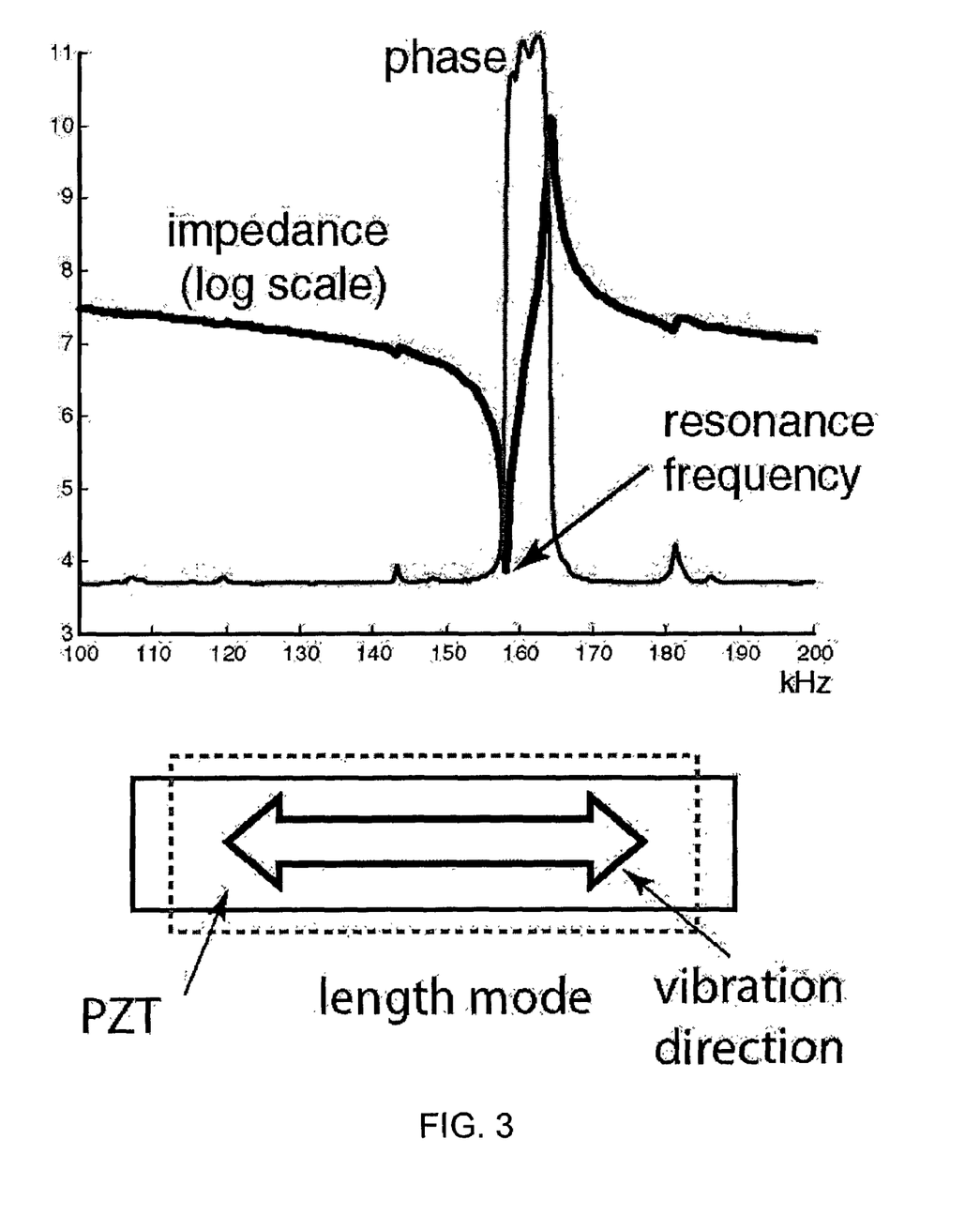
FIG. 3 is a graph of measured impedance vs. frequency of a preferred embodiment according to the invention, showing the resonant frequency of the length mode of vibration.
Figure 4:
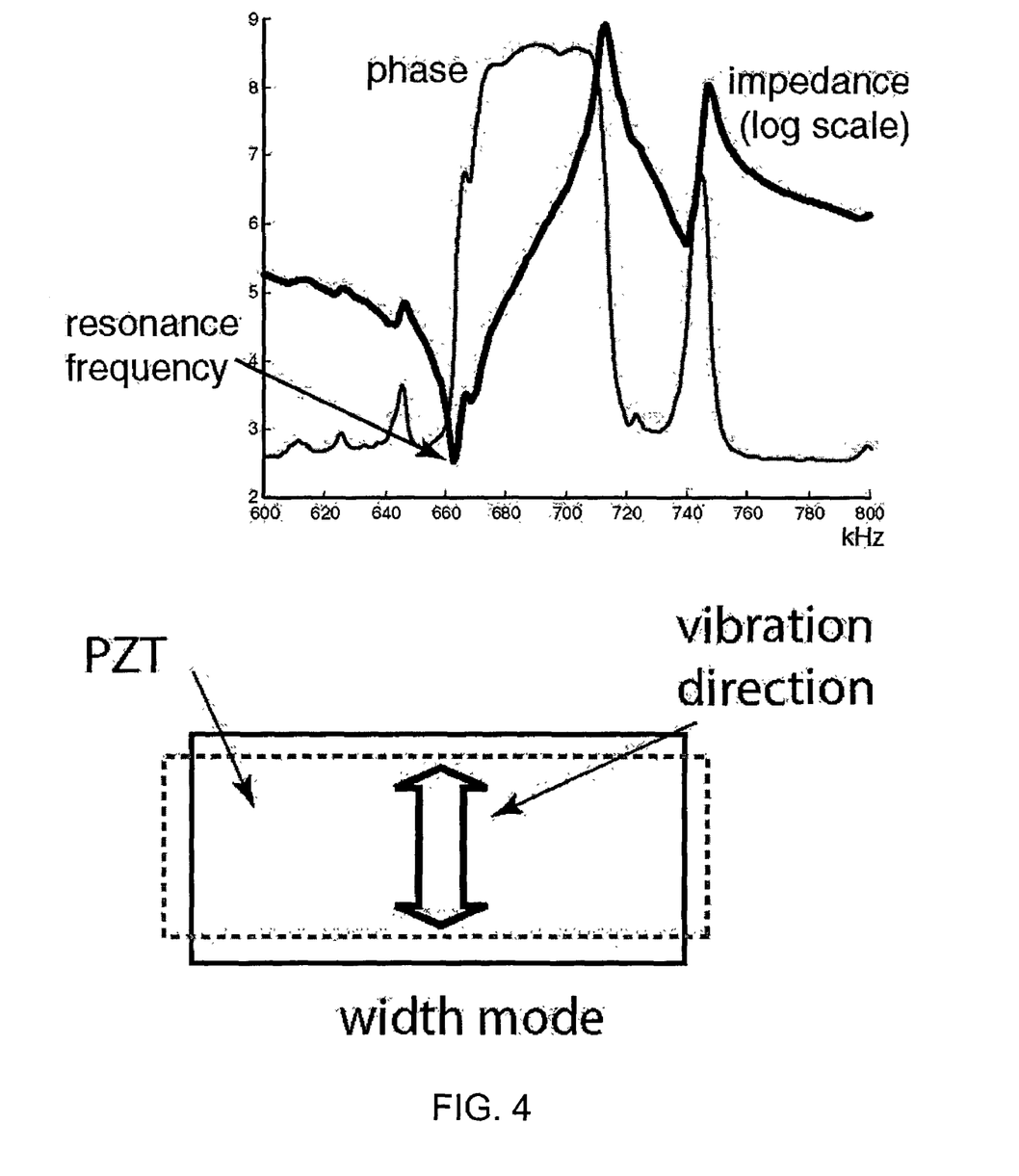
FIG. 4 is a graph of measured impedance vs. frequency of a preferred embodiment according to the invention, showing the resonant frequency of the width mode of vibration.

Eq. 3 predicts a half-wavelength resonance frequency of ~160 kHz for the length mode of the PZT plate of the preferred embodiment shown in FIG. 1. The measured impedance of the λ/2 length mode of vibration is shown in FIG. 3, and the measured impedance of the λ/2 width mode of vibration is shown in FIG. 4. The measured resonance frequencies of the length and width modes of the complete apparatus of FIG. 1 are slightly different from the predicted resonance frequencies of the PZT plate alone using Eq. 3, due to the glass capillary loading effect.

The motion of the glass capillary in the preferred embodiment shown in FIG. 1 has two components which can be analyzed separately. The first component of the motion is a bending motion of the capillary at resonance which can be approximated as a sinusoid, as discussed in more detail below. The second component of the motion comes from the motion of the acoustic transducer (the PZT plate) to which the capillary is attached. The overall motion of the capillary is the sum of these two components.

An exact analysis of the first component (the bending motion) of the capillary motion would require consideration of the finite radius of curvature of the bent glass capillary beam, but in a first analysis the bent capillary can be modeled as a straight beam. The bending motion of a straight beam can be modeled by $$EI\frac{\partial^4 u}{\partial x^4} = \rho A \frac{\partial^2 u}{\partial t^2} \quad (4)$$

where E is the Young's modulus of the glass capillary, I is the moment of inertia, ρ is the density, A is the cross section area, and u is the displacement. The standing wave solutions to Eq. 4 can be written as $$u(X) = C_1 \sin h(kx) + C_2 \cos h(kx) + C_3 \sin(kx) + C_4 \cos(kx) \quad (5)$$

Figure 5:
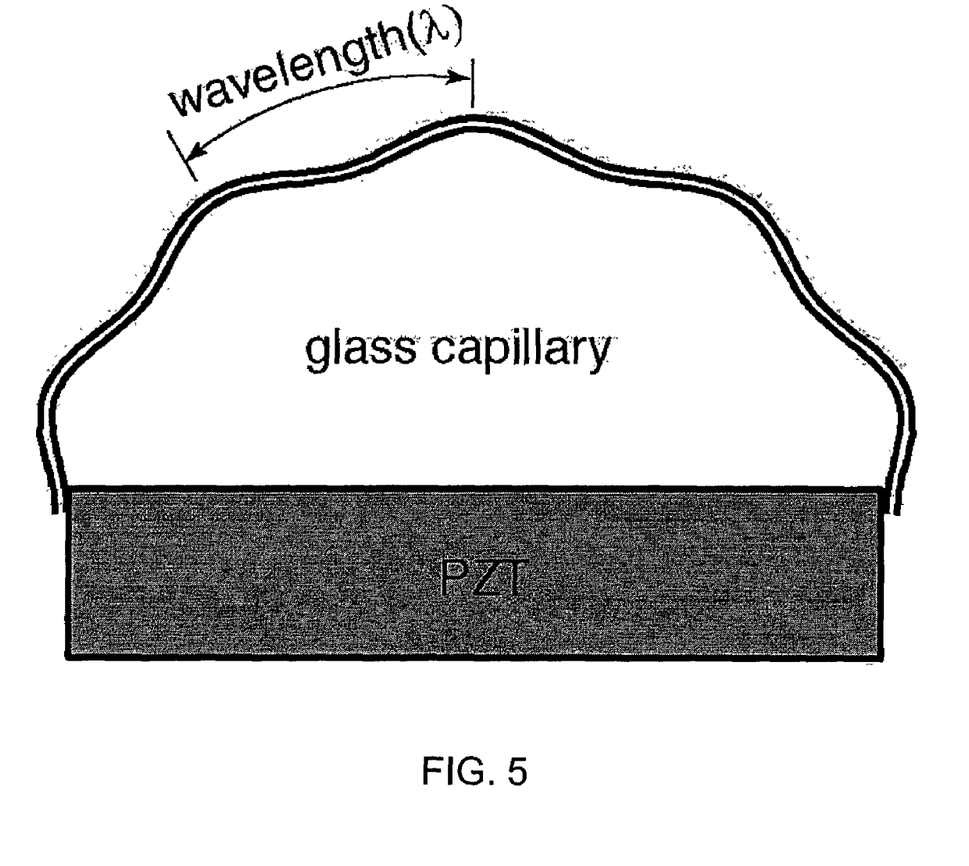
FIG. 5 is a side view of the curved section of the glass capillary found in a preferred embodiment according to the invention, showing a bending mode of the glass capillary.

For the clamped-clamped beam, the sin(km) dominates while the sinh(kx) satisfies boundary conditions at the clamped edges, resulting in a motion which is approximately sin(kx), as illustrated in FIG. 5. Thus, if the glass capillary is resonated at its bending mode resonance frequencies, this first component of the motion of the glass capillary can be approximated as:

$$\upsilon_{y,ac} \sim \sin(kx) \quad (6)$$

The second component of the motion of the glass capillary comes from the motion of the PZT plate. The PZT plate motion induces the following approximate motion to the capillary, $$\upsilon_x \sim x/L - \tfrac{1}{2} \quad (7)$$

$$\upsilon_{y,dc} \sim -x \cdot (x-L) \quad (8)$$

where L is the length of the capillary and the PZT plate edge is located at x=0.

Figure 6:
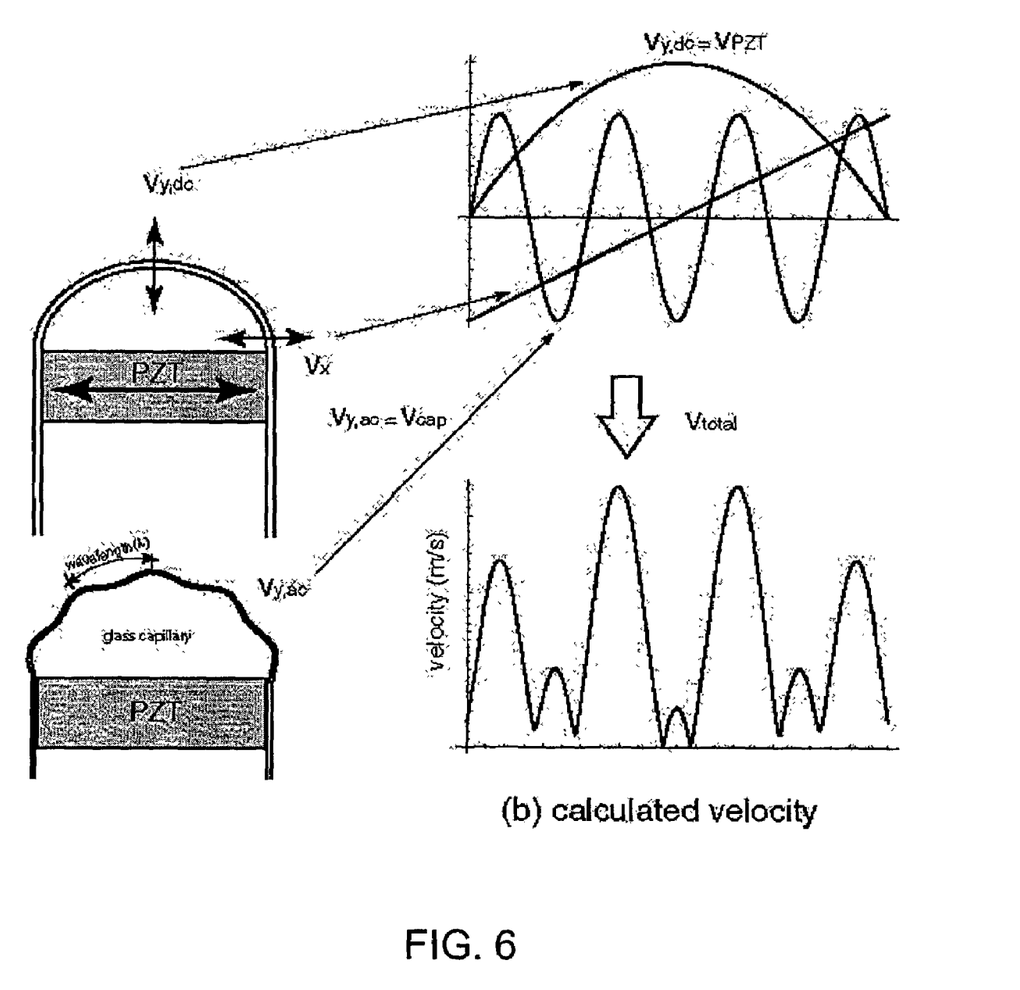
FIG. 6 is a graph showing three components of the calculated velocity of the glass capillary, and the resulting total calculated velocity of the glass capillary.

FIG. 6 illustrates how, if the capillary is resonated at its bending mode resonance frequencies, the total glass capillary velocity in the y direction may be written as the sum of the second component of the motion (given by Eq. 8) and the first component of the motion (given by Eq. 6) as:

$$\upsilon_{y,total} = A_1 \cdot x \cdot (x-L) + B_1 \cdot \sin(kx) \quad (9)$$

where $A_1$ and $B_1$ are constants determined by device dimensions, material properties and driving frequency.

When the transverse motion of the capillary is excited over a wide range of frequencies, this motion induces a force given by $$F_{inertial} = \frac{\pi^2}{4} M u_0^2 \omega^2 k_{cap} \sin(2k_{cap} x) \quad (10)$$

where $$M\left(=\frac{4\pi}{3}d^3(\rho_{bead} - \rho_{water})\right)$$

is the mass difference between the bead and water, $u_0$ is the transverse displacement amplitude, ω is the radian frequency, and $k_{cap}$ is the wavenumber corresponding to the capillary mode.

Figure 7:
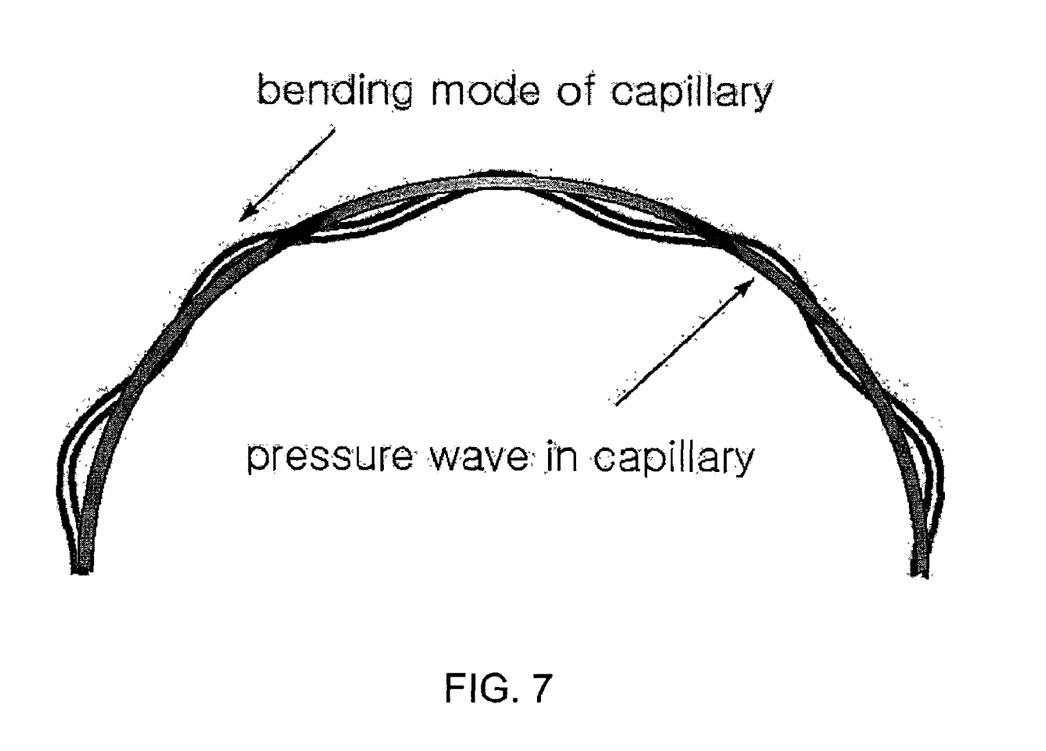
FIG. 7 is a side view of the curved section of the glass capillary found in a preferred embodiment according to the invention, showing a pressure wave in the capillary and a bending mode of the glass capillary.
Figure 8:
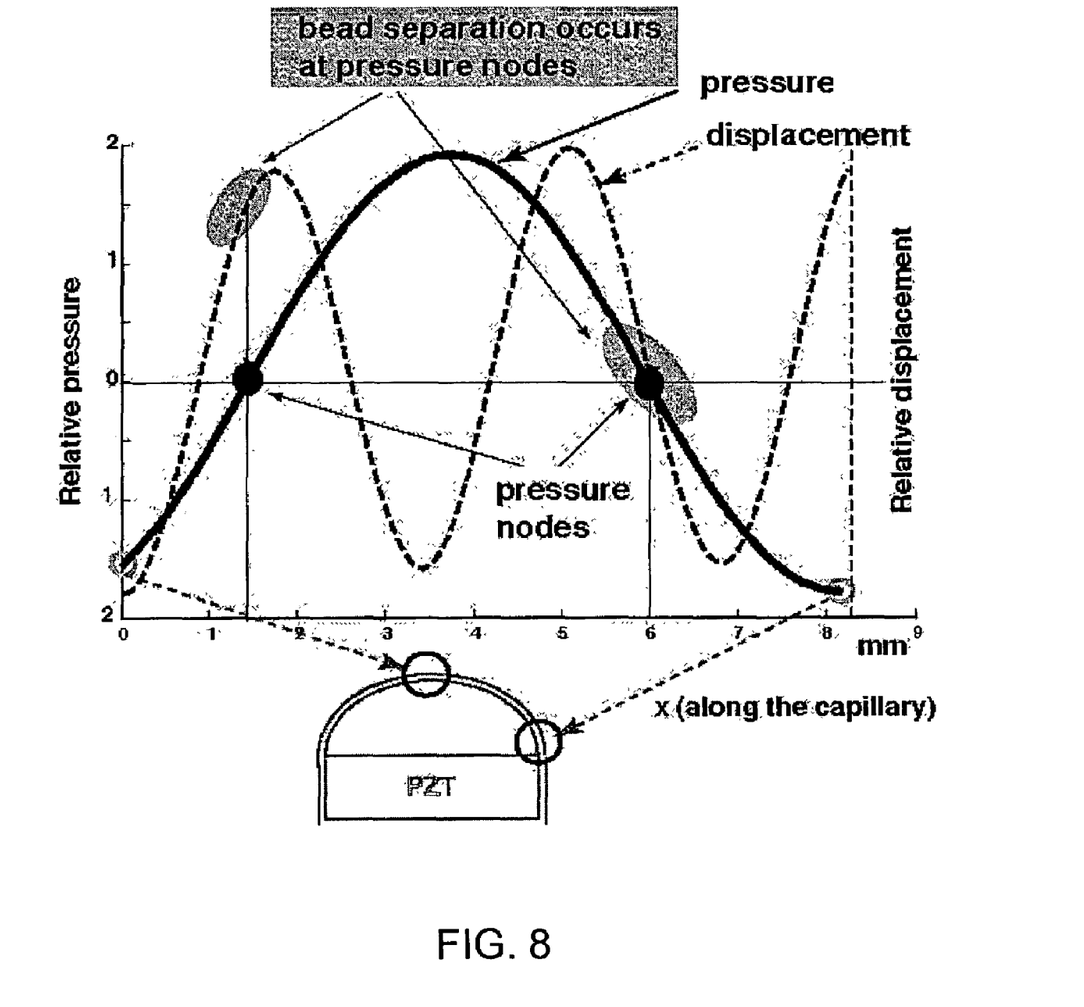
FIG. 8 is a graph of the pressure profile of a pressure wave in the capillary superimposed on the displacement profile of a bending mode of the capillary.

However, this inertial force alone randomizes the bead motion and separation is not achieved. To separate, a radiation force along the capillary is needed. The x-directed velocity $\upsilon_x$ supplied by the PZT motion, approximated as a straight line in FIG. 6, supplies this radiation force. The PZT stretches the capillary exciting the symmetric acoustic pressure standing waves inside the capillary. FIG. 7 illustrates the bending motion of the capillary superimposed on the pressure standing waves inside the capillary. FIG. 8 shows the pressure profile inside the capillary superimposed on the displacement profile of the capillary.

Figure 9:
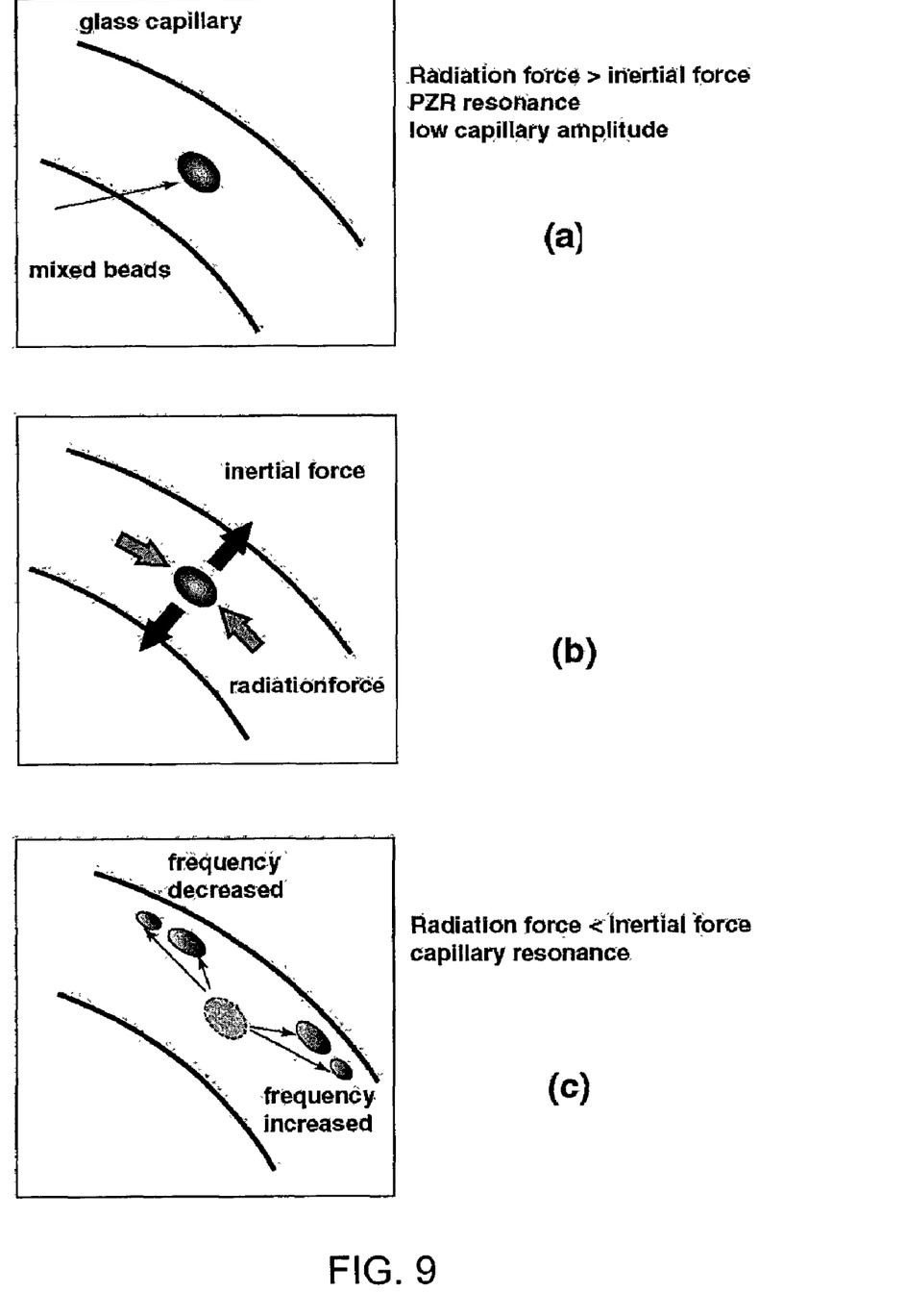
FIG. 9 is an illustration of the forces operating on suspended particles during operation of a preferred embodiment according to the invention.

FIG. 9 shows how the inertial and radiation forces may be adjusted to achieve separation in a preferred embodiment according to the invention. At PZT resonance, the radiation force of the standing pressure wave inside the capillary acting axially is sufficient to overcome the inertial forces described by Eq. 10 to focus particles of all sizes at the pressure nodes, as predicted by Eq. 2 and illustrated in FIG. 9(a). FIG. 9(b) illustrates the directions of the radiation and inertial forces.

As the frequency is changed slightly around the resonance frequency, the radiation force is reduced and the inertial force acting in different directions separates the beads at different angles, as illustrated in FIG. 9(b)–(c). As the frequency is increased or decreased, the inertial force vector changes giving separated beads in two different angles as shown in FIG. 9(c). Hence, bead separation is enabled by application of radiation and inertial forces acting in different directions with controlled amplitudes. The inertial force is maximized at the points of maximum slope of the capillary transverse motion, close to the points of stable points of radiation force. Two such points are shown in FIG. 8, which were verified by experiments.

Thus it can be seen that the present invention enables separation of particles by size at reduced cost, with lowered power or voltage requirements, with lowered sample volume requirements, and with improved manufacturability, reliability, measurement quality, and response time. While the foregoing description contains many specificities, these should not be construed as limitations on the scope of the invention, but rather as an exemplification of one or more preferred embodiments thereof. Many other variations are possible.

For example, the vessel is preferably but not necessarily a glass capillary tube capable of containing an acoustic medium in which a mixture of different size particles may be suspended. The acoustic medium could be contained in other types of vessels, made of different materials or having different shapes or dimensions, without departing from the spirit of the invention. The vessel may have a cross-section which is not circular, for example a square or rectangular cross-section may be used, and the vessel may be made in a range of sizes. The vessel may be made of materials other than glass, or made of a combination of materials. The vessel may be formed into a greater or lesser portion of a circle, it may be straight, it may be formed into a loop or knot, or it may have some other shape. Although the material of the vessel is preferably at least partially transparent, so that particle aggregation and separation can be visually observed through the walls of the vessel, this is not required.

Although in a preferred embodiment, a standing pressure wave in the vessel may be used to aggregate particles of all sizes at pressure nodes within the vessel, other forces may be applied for this purpose. For example, the particles may be aggregated using electrostatic or centrifugal forces prior to separation.

Although in a preferred embodiment a standing pressure wave in the vessel may be created by applying a first acoustic field with energy at a single frequency at or near a first resonant frequency corresponding to a longitudinal resonance of the first acoustic transducer, other types of first acoustic fields may be applied to aggregate the mixture of particles without departing from the spirit of the invention. For example, the first acoustic field could contain energy at multiple frequencies, for example a square wave, triangle wave, or other complex waveform, or the first acoustic field could contain energy at a range of frequencies where the energy distribution varies as a function of time, for example frequency modulated or "chirp" pressure variations. The optimal characteristics of the first acoustic field will depend on boundary conditions placed on the acoustic medium, for example by the shape and dimensions of the vessel containing the acoustic medium, on characteristics of the acoustic medium itself, such as the density and speed of sound in the acoustic medium, on characteristics of the particles to be separated, such as their mass and size, and other factors, for example the desired separation speed and precision. Depending on the characteristics of the first acoustic field, a standing pressure wave may or may not be formed, and the mixture of different size particles may aggregate at positions other than pressure nodes in a standing pressure wave.

Although in a preferred embodiment, a single acoustic transducer is used to aggregate the particles and to separate the particles, the apparatus according to the invention may have two or more acoustic transducers, which may be but are not necessarily piezoelectric plates. For example, a first acoustic transducer may be used to induce the aggregation, while a second acoustic transducer may be used to separate the particles by size.

Although in a preferred embodiment, application of the second acoustic field may excite transverse vibrations in the vessel to separate the particles by size, other types of forces or motions could be used for this purpose. Any force which varies according to the size of each particle could be used to cause the aggregated mixture of different size particles to be separated by size.

Although in a preferred embodiment the second acoustic field may contain energy at a single frequency at or near a second resonant frequency corresponding to a resonance of the vessel, other types of second acoustic fields could be used to apply a force to separate the particles by size without departing from the spirit of the invention. For example, the second acoustic field could contain energy at multiple frequencies, for example a square wave, triangle wave, or other complex waveform, or the second acoustic field could contain energy at a range of frequencies where the energy distribution varies as a function of time, for example frequency modulated or "chirp" waveforms. The optimal characteristics of the second acoustic field will depend on boundary conditions placed on the acoustic medium, for example by the shape and dimensions of the vessel containing the acoustic medium, on characteristics of the acoustic medium itself, such as the density and speed of sound in the acoustic medium, on characteristics of the particles to be separated, such as their mass and size, and other factors, for example the desired separation speed and precision. Depending on the characteristics of the second acoustic field, transverse vibrations in the vessel may or may not be formed, and the second acoustic field may or may not be applied in a direction which is roughly orthogonal to the direction of propagation of the pressure variations of the first acoustic field.

Although in a preferred embodiment, the relative magnitudes of the aggregating and separating forces are adjusted by changing the frequency of the first acoustic field away from a first resonant frequency, the relative magnitudes can be adjusted in other ways without departing from the spirit of the invention. The first acoustic field can be adjusted in other ways, for example by changing the direction or amplitude of the first acoustic field. Alternatively, the second acoustic field can be adjusted, for example by changing the frequency, direction or amplitude of the second acoustic force. Finally, both the first and the second acoustic fields can be adjusted to adjust the relative magnitudes of the aggregating and separating forces.

Although in a preferred embodiment the first acoustic field may be applied while the second acoustic field is applied, this is not necessarily so. In a "pulsed" mode embodiment, the first acoustic field could be discontinued entirely once the mixture of different size particles aggregates at a location, with the second acoustic field applied as a separate step to separate the particles following aggregation.

Alternatively, the first and second acoustic fields can be combined into a single acoustic field with time-varying characteristics, which can be applied to first aggregate a mixture of different sized particles and then separate that mixture of particles by size.

In a preferred embodiment, the first and second acoustic transducers may be comprised of a single piezoelectric plate, for example formed of lead zirconate titanate (PZT). The first and second acoustic transducers which produce the first and second acoustic fields may be formed in other ways without departing from the spirit of the invention. Separate piezoelectric plates can be used for the first and second acoustic transducers, and more than one piezoelectric plate can be used for each of the first and second acoustic transducers. Other piezoelectric materials, such as zinc oxide or lithium niobate, could be used instead of PZT. Other types of acoustic transducers may be used to create either or both of the first and second acoustic fields, in place of or in addition to the one or more piezoelectric plates.

It is understood that the invention is not confined to the embodiments set forth herein as illustrative, but embraces all such forms thereof as come within the scope of the following claims.

What is claimed is:

1. An apparatus for separating by size particles suspended in an acoustic medium, comprising:
    (a) a vessel;
    (b) an acoustic medium in the vessel; and
    (c) at least one ultrasound transducer for applying a longitudinal acoustic field in a first direction to the acoustic medium in the vessel to aggregate the particles in the medium and a second acoustic field in a second direction to separate the particles by size, wherein the second direction is transverse to the longitudinal direction.

2. The apparatus of claim 1 wherein at least a portion of the vessel is curved around at least a portion of at least one ultrasound transducer.

3. The apparatus of claim 1 wherein at least a portion of the vessel is formed in a loop around at least a portion of at least one ultrasound transducer.

4. The apparatus of claim 1 wherein the at least one ultrasound transducer comprises a single ultrasound transducer for applying both the first acoustic field and the second acoustic field to the acoustic medium in the vessel.

5. The apparatus of claim 1 wherein the at least one ultrasound transducer comprises a first ultrasound transducer for applying the first acoustic field and a second ultrasound transducer for applying the second acoustic field.

6. The apparatus of claim 1 wherein the vessel comprises a glass capillary tube.

7. The apparatus of claim 6 wherein at least a portion of the vessel is curved around at least a portion of at least one ultrasound transducer.

8. The apparatus of claim 6 wherein the vessel is formed in a loop around at least a portion of at least one ultrasound transducer.

9. The apparatus of claim 6 wherein the at least one ultrasound transducer comprises a single ultrasound transducer for applying both the first acoustic field and the second acoustic field to the acoustic medium in the vessel.

10. The apparatus of claim 6 wherein the first acoustic field creates a standing pressure wave in at least a portion of the vessel.

11. A method of separating by size a mixture of particles of various sizes comprising:
    (a) suspending the mixture of particles of various sizes in an acoustic medium in a tube;
    (b) applying a first acoustic radiation in a longitudinal direction in the tube to create a standing pressure wave in at least a portion of the acoustic medium thereby forming an aggregate of the mixture of particles of various sizes near a node of the standing pressure wave; and
    (c) applying a second acoustic radiation in a transverse direction in the tube to separate the particles by size
    whereby the aggregate of the mixture of particles of various sizes is separated by size.

12. The method of claim 11 wherein at least a portion of the tube is curved.

13. The method of claim 11 wherein at least a portion of the tube is formed in a loop.

14. The method of claim 11 wherein a piezoelectric plate is used to apply at least a portion of the first acoustic radiation.

15. The method of claim 11 further comprising the step of increasing the intensity of the first acoustic radiation.

16. The method of claim 11 further comprising the step of increasing the frequency of the first acoustic radiation.

17. The method of claim 11 further comprising the step of decreasing the intensity of the first acoustic radiation.

18. The method of claim 11 further comprising the step of decreasing the frequency of the first acoustic radiation.

19. The method of claim 11 wherein the tube comprises a glass capillary tube.

20. The method of claim 19 wherein at least a portion of the tube is curved.

21. The method of claim 19 wherein at least a portion of the tube is formed in a loop.

22. The method of claim 19 wherein a piezoelectric plate is used to apply at least a portion of the first acoustic radiation.

23. The method of claim 19 further comprising the step of increasing the intensity of the first acoustic radiation.

24. The method of claim 19 further comprising the step of increasing the frequency of the first acoustic radiation.

25. The method of claim 19 further comprising the step of decreasing the intensity of the first acoustic radiation.

26. The method of claim 19 further comprising the step of decreasing the frequency of the first acoustic radiation.

* * * * *